US007065408B2

(12) United States Patent
Herman et al.

(10) Patent No.: US 7,065,408 B2
(45) Date of Patent: Jun. 20, 2006

(54) METHOD FOR RESTORING GAIT IN INDIVIDUALS WITH CHRONIC SPINAL CORD INJURY

(76) Inventors: Richard M. Herman, 11999 N. 114th Way, Scottsdale, AZ (US) 85259; Stephen C. D'Luzansky, 14613 S. 32nd St., Phoenix, AZ (US) 85044; Jiping He, 1449 W. Amanda La., Tempe, AZ (US) 85284; James D. Sweeney, 1251 E. Sunburst La., Tempe, AZ (US) 85284

( * ) Notice: Subject to any disclaimer, the term of this patent is extended or adjusted under 35 U.S.C. 154(b) by 223 days.

(21) Appl. No.: 10/041,320

(22) Filed: Jan. 8, 2002

(65) Prior Publication Data

US 2002/0115945 A1 Aug. 22, 2002

Related U.S. Application Data

(60) Provisional application No. 60/261,055, filed on Jan. 11, 2001.

(51) Int. Cl.
*A61N 1/08* (2006.01)
(52) U.S. Cl. ............................ 607/49; 607/117; 482/54
(58) Field of Classification Search ............ 607/48–49, 607/77–78, 117; 482/54
See application file for complete search history.

(56) References Cited

U.S. PATENT DOCUMENTS 5,002,053 A    3/1991  Garcia-Rill et al.
5,843,142 A *  12/1998 Sultan ........................ 607/49
5,961,541 A *  10/1999 Ferrati ........................ 607/49

OTHER PUBLICATIONS

"Spinal cord Stimulation Facilitates Walking in a Chronic, Incomplete Spinal Cord Injured,", Spinal Cord. Feb. 2002; 40(2):65-8, Herman et al.*
"Epidural Spinal-Cord Stimulation Facilitates Recovery of Functional Walking Following Incomplete Spinal-Cord Injury", IEEE Transactions on Neural Systems and Rehabilitation Engineering, vol. 12, No. 1 Mar. 2004 Carhart et al.*
"Combined Use of Body Weight Support, Functional Electric Stimulation, and Treadmill Training to Improve Walking Ability in Individuals With Chronic Incomplete Spinal Cord Injury", Arch Phys Med Rehabil vol. 82, Jun. 2001, Field-Foote.*
"Locomotor Therapy in Neurorehabilitation", NeuroRehabilitation 2001; 16(3): 133-9.*

* cited by examiner

*Primary Examiner*—Mark Bockelman
(74) *Attorney, Agent, or Firm*—Snell & Wilmer L.L.P.

(57) ABSTRACT

A method for restoring functional ambulation in subjects with incomplete spinal cord injuries which includes partial weight bearing therapy followed by epidural spinal cord stimulation (ESCS) to facilitate partial weight bearing therapy and over-ground walking. Electrical epidural stimulation (EES) is generated by an implanted device during partial weight bearing therapy on a treadmill. The subject is then transitioned to full weight bearing gait training on a treadmill with EES to over-ground gait training with EES and a walker, and finally to full weight bearing independent stepping over-ground with EES with or without an assistive device.

9 Claims, 2 Drawing Sheets

METHOD FOR RESTORING GAIT IN INDIVIDUALS WITH CHRONIC SPINAL CORD INJURY

CROSS-REFERENCE TO RELATED APPLICATION

This application claims the benefit of, and priority to, U.S. provisional application Ser. No. 60/261,055, filed Jan. 11, 2001, which application is hereby incorporated by reference in its entirety.

FIELD OF INVENTION

The present invention generally relates to a method for restoring gait in individuals having spinal cord injuries. More particularly, the present invention relates to a method for restoring functional ambulation in individuals having incomplete spinal cord injuries which includes partial weight bearing therapy followed by epidural spinal cord stimulation to facilitate partial weight bearing therapy and over-ground walking.

BACKGROUND OF THE INVENTION

Among the approximately 250,000 spinal cord injured (SCI) in the United States, there is a considerable population of chronic incomplete spinal cord injuries (ISCI) who are designated as ASIA B (some sensory sparing and abolished motor power) or C (some sensory sparing and sub-functional motor power) in the lower extremities. Generally, they are wheelchair-dependent, although they may be able to stand or even take a few crude steps for exercise, but are not consistent functional ambulators at home or within the community.

Two novel strategies have been individually employed to augment locomotion rhythm generation, making use of the adaptability and capacity for retraining/learning of spinal cord circuits: partial weight bearing therapy (PWBT) and epidural spinal cord stimulation (ESCS). PWBT has evolved from observations of chronic spinal animals, whereby moving a treadmill can initiate and sustain locomotion when the body is supported. (See Muir GD, Steeves JD, "Sensorimotor Stimulation to Improve Locomotor Recovery After Spinal Cord Injury", *TINS* 1997, volume 20, pages 72–77.) As a consequence, various afferent inputs into the intrinsic spinal circuitry contribute to a coordinated locomotion pattern with state-dependent and phase-dependent reflexes. It is well respected that PWBT facilitates functional walking among chronic ASIA D (significant functional motor power) patients. To our knowledge, there are no publications documenting the effect of PWBT among ASIA B and ASIA C patients with regard to transitioning treadmill walking to restoration of functional ambulation in terms of household or community walking.

Non-patterned ESCS, which modulates segmental spinal and/or brain stem-spinal pathways in the ISCI, has also shown potential in initiating and sustaining locomotion among Multiple Sclerosis and ASIA D patients. ESCS at the lumbar enlargement in animals, with low frequency, long pulse duration, and supramotor threshold current intensity, induces hind-limb locomotion patterns following an acute mid-thoracic spinal cord transection. (See Iwahara T, Atsuta Y, Garcia-Rill E, Skinner RD, "Spinal Cord Stimulation-Induced Locomotion in the Adult Cat", *Brain Res Bull* 1992, pages 99–105.) These parameters, however, contrast with Dimitrijevic's observations in acute human experiments with clinically complete SCI in a supine position. (See Dimitrijevic MR, Gerasimenko Y, Pinter MM, "Evidence for a Spinal Central Pattern Generator in Humans", *Ann N Y Acad Sci* 1998; volume 860: pages 360–376.)

A need presently exists for a method for restoring functional ambulation in individuals having incomplete spinal cord injuries so that these individuals can achieve functional non-assisted walking in their households and communities.

SUMMARY OF THE INVENTION

The present invention is directed to a method for restoring functional ambulation in subjects having incomplete spinal cord injuries which includes the combined steps of providing partial weight bearing therapy until a subject reaches a plateau in locomotion rhythm generation and electrically stimulating the spinal cord with an implanted stimulation device.

In one aspect of the invention, the step of providing partial weight bearing therapy includes the step of achieving partial weight bearing gait performance on a treadmill with or without one or more therapists moving the subject's legs and the partial weight bearing gait performance includes transition on the treadmill from one weight bearing/treadmill rate level (therapeutic level) to another.

The subject is transitioned across a number of therapeutic levels, after meeting a predetermined set of criteria, until reaching a final gait performance which is followed by the step of electrically stimulating the spinal cord with an implanted stimulation device. In one aspect of the invention, the predetermined set of criteria for transferring to the next therapeutic level include achieving an alternating gate with no more than 50% asymmetry, overcoming the need for any assistance by a therapist for three sixty second periods on the same day for three consecutive days, and achieving a existence of a breakdown of the gait performance criteria at a higher weight/treadmill rate (therapeutic level).

The final gate performance is determined at a specific degree of weight bearing and treadmill rate that continually produces breakdown of the gait over a four week period.

In one exemplary embodiment of the method of the present invention, the step of electrically stimulating the spinal cord includes the steps of surgically implanting a spinal cord stimulating device in the subject and providing gait training with electrical epidural stimulation generated by the stimulating device. The step of providing gait training with electrical epidural stimulation may include the steps of providing partial weight bearing gait training on a treadmill with electrical epidural stimulation (EES) to full weight bearing gait training on a treadmill with EES and over ground with EES with a walker to further refine stimulus patterns, and achieving full weight bearing independent stepping over ground without a harness with EES.

BRIEF DESCRIPTION OF THE DRAWINGS

Additional aspects of the present invention should become evident upon reviewing the non-limiting embodiments described in the specification taken in conjunction with the accompanying figures where.

DETAILED DESCRIPTION

Figure 1:
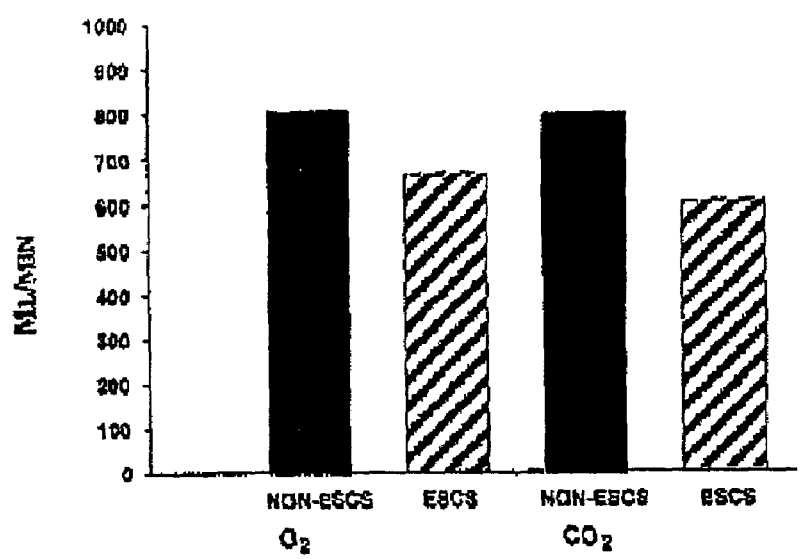
FIG. 1A is a bar graph showing gas exchange data for a patient walking a same distance under epidural spinal cord stimulation (ESCS) and non-epidural (non-ESCS) spinal cord stimulation during an early training stage in the method of the present invention.
FIG. 1B is a bar graph showing the respiratory exchange ratio (RER; $VCO_2/VO_2$) elicited by activated muscles of a patient used during walking during both ESCS and non-ESCS.
Figure 1:
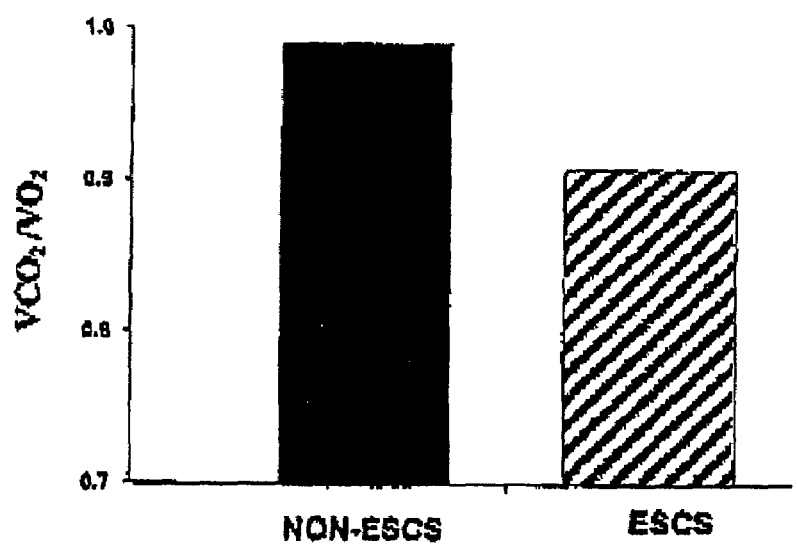

In general, the present invention is directed to a method for restoring gait in individuals with chronic spinal cord injury. The method for restoring functional ambulation in subjects having incomplete spinal cord injuries includes the step of providing partial weight bearing therapy until a subject reaches a plateau in locomotion rhythm generation followed by the step of electrically stimulating the spinal cord with an implanted stimulation device. After implantation of the stimulation device, gait training is performed with electrical epidural stimulation generated by the stimulating device. Gait training with electrical stimulation may include providing partial weight bearing gait training on a treadmill with EES to investigate stimulus patterns, transitioning from partial weight bearing gait training on a treadmill with EES and over ground EES with a walker to further refine stimulus patterns, and achieving full weight bearing independent stepping over ground without a harness with EES.

The method of the present invention for restoring gait in individuals with incomplete chronic spinal cord injury was achieved with the following methodology and results:

Methods

The Institutional Review Board of the two institutions approved the study and written informed consent was obtained from the subject. A 43-year-old male subject with C5–6 ISCI (ASIA C) quadriplegia (3.5 years post injury) was recruited. PWBT was performed using the LiteGait™ system (Mobility Research, Tempe, Ariz.). Under the guidance of physical therapists, the subject underwent progressive training with increasing treadmill rates and degree of weight bearing until he demonstrated a plateau in performance.

A pair of Pisces-Quadplus electrodes (in combination with the X-TREL stimulation system by Medtronic Inc., Minneapolis, Minn.) were inserted into the dorsal epidural space over the upper lumbar enlargement of the spinal cord. After surgical wound healing and retraining with PWBT to pre-surgery levels, a variety of electrical parameter sets were examined to test the efficacy of ESCS to enhance locomotion performance. Locomotion characteristics were analyzed by measuring average speed, stepping symmetry, swing/stance times, sense of effort (approximating the Borg Scale), physical work capacity, and whole body metabolic activity.

Results

PWBT led to an improved stereotypic stepping pattern on the treadmill and during an over-ground 15 m walk with extremely low speed, poor endurance, and a marked sense of effort (8/10). After combining PWBT and ESCS, immediate improvements were noted: a propensity to exhibit a smoother, more organized stepping pattern at higher treadmill rates and self-supported body weight, considerable improvement in endurance and speed during over-ground walking, and decreased sense of effort (2/10).

Vital ESCS parameters included electrode distance, pulse duration, and amplitude. We observed that long pulse durations (e.g., 0.8 msec) were essential while frequencies (e.g., 20–60 Hz) were comparatively less sensitive. The amplitude was above sensory threshold (sense of "parasthesia or vibration") but below that causing motor contraction. The electrode distance was at least 15 mm to cover a wide segment of the spinal cord lumbar enlargement.

Early in the transition from PWBT to over-ground walking, the gas exchange data revealed that ESCS reduced exercise-induced $CO_2$ and production and $O_2$ consumption rates see FIG. 1A. The subject walked a similar distance (45 m) under ESCS and non-ESCS conditions. The values shown are the exercise-induced (net) increases above resting values which were essentially identical under both conditions. The values suggest that the energy cost for walking this distance is reduced by ~20% for the ESCS condition. The net respiratory exchange ratio or RER ($VCO_2/VO_2$) was markedly reduced by ESCS as shown in FIG. 1B. Under conditions of acid-base balance, the RER is equal to the respiratory quotient (RO). The entire physiological range of RO is 0.70 (all fat oxidation) to 1.00 (all carbohydrate oxidation). With Non-ESCS walking, RER was 0.99, suggesting that fat provided ~3% of the energy, and carbohydrate (CHO) the remaining ~97%. With stimulation, the net RER was 0.907, inferring that fat and CHO provided ~31% and ~69% of the energy, respectively. Thus, about an 8-fold increase in fat oxidation occurred with ESCS.

Figure 2:
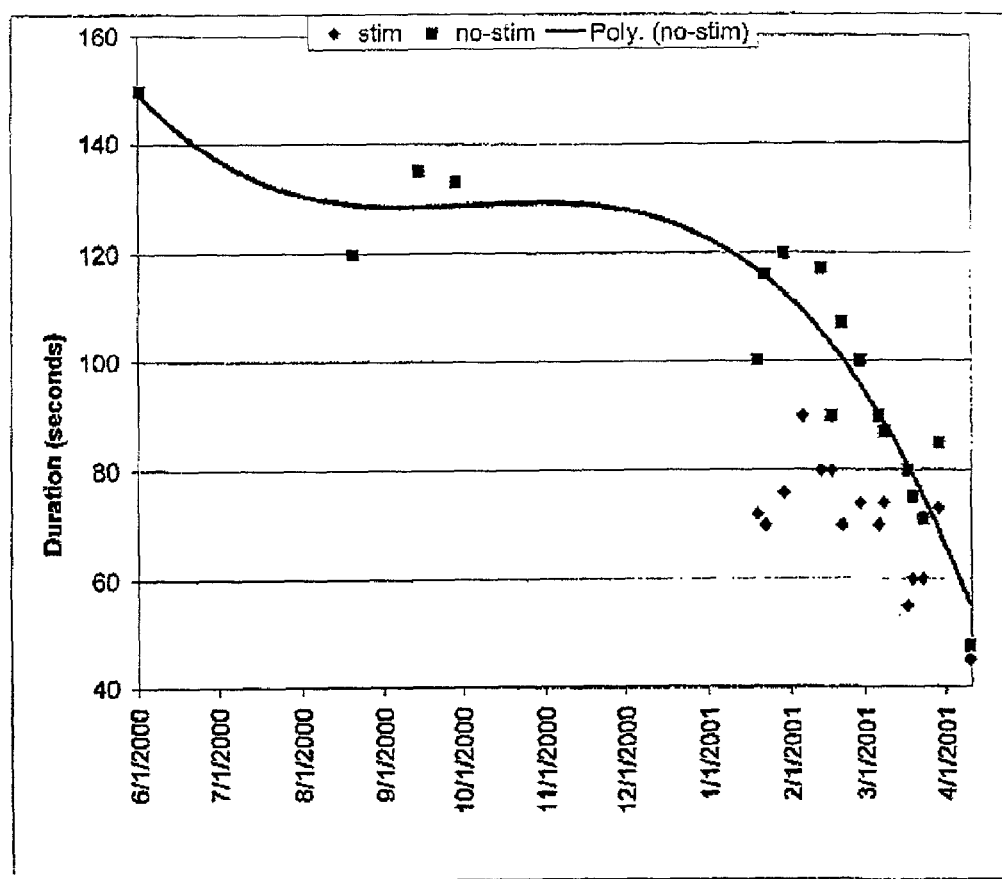
FIG. 2 is a graph showing the duration of time for a patient to traverse a distance of 17 meters at different stages of the method of the present invention.

ESCS was associated with increased walking speed and decreased sense of effort by a factor of three. With 1.5 months of continued training, the average walking speed, gas exchange responses, and endurance converged between the two conditions (ESCS and non-ESCS). The trend line in FIG. 2 demonstrates a continued improvement for the non-ESCS condition. FIG. 2 shows the duration of time for the subject to traverse a distance of 17 meters at different stages of the treatment. After four months of over-ground training, the subject could ambulate 270 m, which enabled him to perform community and homebound functional ambulation.

Discussion

Purportedly, the mechanism of PWBT has been ascribed to the retraining of the spinal cord circuits to promote the sensitivity of the system to generate locomotion rhythm-related signals, within the context of both motor drives and sensory reflexes. When the injury is severe (ASIA B and C), signals from motor drives and sensors are week. Hence, the success of PWBT to promote functional ambulation is difficult to achieve but capable of eliciting a semblance of "use-dependent" behavior during over-ground walking. We theorize that when ESCS is applied in conjunction with PWBT, the electrical current provides the modulation/amplification of neural circuits responsible for locomotion rhythm generation by further exciting segmental afferent inputs and facilitating a "stored" locomotion program.

The gas exchange data indicated that ESCS reduced the $O_2$ and energy cost of walking by ~20%. The impact of ESCS on $CO_2$ production was more pronounced. If acid-base balance during walking is assumed, gas exchange data revealed an 8-fold-greater exercise-induced fat oxidation rate with ESCS (FIG. 1). Alternatively, lower $CO_2$ production during ESCS-assisted walking reflected less accumulation of blood lactate and associated bicarbonate titration. Both interpretations imply that ESCS reduced the dependence of exercising muscle on glycolysis, and hence accounted for the marked improvement in muscle endurance observed in the ESCS condition. We conclude that ESCS may elicit greater activation of an oxidative motor unit pool in the spinal cord via modulating large afferent input (e.g., Ia fibers) which can alter motor unit recruitment pattern (see Burke RE, Edgerton VR, "Motor Unit Properties and Selective Involvement in Movement", *Exerc Sport Sci Rev* 1975, volume 3, pages 31–81), thereby reducing the sense of effort (see Granit R, "Constant Errors in the Execution and Appreciation of Movement", *Brain* 1972, volume 95, pages 649–660) and the energetic cost of walking and expanding physical work capacity.

We propose that ESCS augmented the "use-dependent plasticity". Created by PWBT and concur with the view that ESCS "has the potential for serving as a valuable adjunct to post-SCI treadmill training and other therapeutic interventions" (see "Spinal Cord Stimulation-Induced Locomotion in the Adult Cat", id.) Although the results reported here are derived from only one subject, it is clear that the combined PWBT and ESCS therapy can facilitate restoration of functional ambulation of a wheelchair-dependent ISCI patient.

The invention claimed is:

1. A method for restoring functional ambulation in subjects having incomplete spinal cord injuries comprising the steps of:
    a. Providing partial weight bearing therapy by achieving partial weight bearing gait performance on a treadmill with or without one or more therapists moving a subject's legs until the subject reaches a plateau in locomotion rhythm generation; and
    b. Electrically stimulating the spinal cord with an implanted stimulation device.

2. The method of claim 1 wherein partial weight bearing gait performance includes transition on the treadmill from one weight bearing/treadmill rate level to another.

3. The method of claim 2 wherein the subject is transitioned across a number of therapeutic levels upon meeting a predetermined set of criteria.

4. The method of claim 3 wherein the predetermined set of criteria include an alternating gait with no more than 50% asymmetry, no assistance by a therapist for 3 sixty second periods on the same day for three consecutive days, and a breakdown of the gait performance criteria at a higher weight/treadmill rate condition.

5. The method of claim 1 wherein partial weight bearing gait performance includes final gait performance which determines eligibility for stimulation.

6. The method of claim 5 wherein final gait performance is determined at a specific degree of weight bearing and treadmill rate that continually produces breakdown of the gait over a four week period.

7. The method of claim 1 wherein the step of electrically stimulating the spinal cord include the steps of:
    a. surgically implanting a spinal cord stimulating device in the subject; and
    b. providing gait training with electrical epidural stimulation generated by the stimulating device.

8. The method of claim 7 wherein the step of providing gait training with electrical epidural stimulation comprises the steps of:
    a. providing partial weight bearing gait training on a treadmill with electrical epidural stimulation (EES) to investigate stimulus patterns;
    b. transitioning from partial weight bearing gait training on a treadmill with EES to full weight bearing gait training on a treadmill with EES and over ground with EES with a walker to further refine stimulus patterns; and
    c. achieving full weight bearing independent stepping over ground without a harness with EES.

9. The method of claim 8 wherein the step of achieving full weight bearing independent stepping is done with or without an assistive device.

\* \* \* \* \*